United States Patent
Sakai et al.

(10) Patent No.: US 11,324,482 B2
(45) Date of Patent: May 10, 2022

(54) ULTRASOUND DIAGNOSTIC APPARATUS

(71) Applicant: Konica Minolta, Inc., Tokyo (JP)

(72) Inventors: Takashi Sakai, Yokohama (JP);
Takashi Kimoto, Yokohama (JP);
Akihiro Kawabata, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 252 days.

(21) Appl. No.: 16/248,005

(22) Filed: Jan. 15, 2019

(65) Prior Publication Data
US 2019/0216429 A1    Jul. 18, 2019

(30) Foreign Application Priority Data

Jan. 16, 2018  (JP) .............................. JP2018-004649

(51) Int. Cl.
*A61B 8/00* (2006.01)
*A61B 8/14* (2006.01)
*A61B 8/08* (2006.01)

(52) U.S. Cl.
CPC .......... *A61B 8/4494* (2013.01); *A61B 8/0841* (2013.01); *A61B 8/145* (2013.01);
(Continued)

(58) Field of Classification Search
CPC ... A61B 8/4494; A61B 8/4455; A61B 8/0841; A61B 8/466; A61B 8/5246; A61B 8/145;
(Continued)

(56) References Cited

U.S. PATENT DOCUMENTS

2012/0108974 A1* 5/2012 Katou ................... A61B 8/461
                                                               600/445
2014/0046187 A1* 2/2014 Taniguchi ........... A61B 8/4461
                                                               600/444
(Continued)

FOREIGN PATENT DOCUMENTS

JP        H08299337 A    11/1996
JP         09313491 A    12/1997
(Continued)

OTHER PUBLICATIONS

JPO Notice of Reasons for Refusal for corresponding JP Application No. 2018-004649; dated May 25, 2021.
(Continued)

*Primary Examiner* — Joseph M Santos Rodriguez
*Assistant Examiner* — Kaitlyn E Selmer
(74) *Attorney, Agent, or Firm* — Cantor Colburn LLP

(57) ABSTRACT

An ultrasound diagnostic apparatus includes an ultrasound probe including a plurality of transducers arranged in a plurality columns and a switching element which switches input of a driving signal to the transducers and output of a receiving signal, a transmitter which outputs the driving signal to the transducers, a receiver which acquires the receiving signal corresponding to the transducers, and a hardware processor which generates ultrasound image data corresponding to each of the columns from the receiving signal, makes partial images in the ultrasound image data respectively have representations, synthesizes the ultrasound image data respectively including the partial images to generate composite image data, generates first identification information indicating to which position in a depth direction of the composite image data each of the representations of the partial images in the composite image data (Continued)

corresponds, and displays the generated first identification information and composite image data on a display.

10 Claims, 8 Drawing Sheets

(52) U.S. Cl.
CPC .......... *A61B 8/4455* (2013.01); *A61B 8/4461* (2013.01); *A61B 8/463* (2013.01); *A61B 8/466* (2013.01); *A61B 8/5207* (2013.01); *A61B 8/5246* (2013.01); *A61B 8/085* (2013.01); *A61B 8/467* (2013.01); *A61B 8/5215* (2013.01); *A61B 8/54* (2013.01)

(58) Field of Classification Search
CPC ..... A61B 8/4461; A61B 8/5207; A61B 8/463; A61B 8/54; A61B 8/467; A61B 8/5215; A61B 8/085
See application file for complete search history.

(56) References Cited

U.S. PATENT DOCUMENTS

| 2016/0014344 | A1* | 1/2016 | Yoo ........................ A61B 8/467 |
| | | | 345/420 |
| 2017/0074837 | A1* | 3/2017 | Lee ......................... A61B 90/36 |
| 2017/0360412 | A1* | 12/2017 | Rothberg ............. A61B 8/4427 |
| 2018/0125448 | A1* | 5/2018 | Karadayi ................ A61B 8/54 |

FOREIGN PATENT DOCUMENTS

| JP | 2000139926 A | 5/2000 |
| JP | 2003019133 A | 1/2003 |
| JP | 2006326204 A | 12/2006 |
| JP | 2010017556 A | 1/2010 |
| JP | 2016047191 A | 4/2016 |
| JP | 2017192478 A | 10/2017 |
| JP | 2017225645 A | 12/2017 |

OTHER PUBLICATIONS

JPO Final Notification of Reason for Refusal for corresponding JP Application No. 2018-004649; dated Oct. 19, 2021.

* cited by examiner

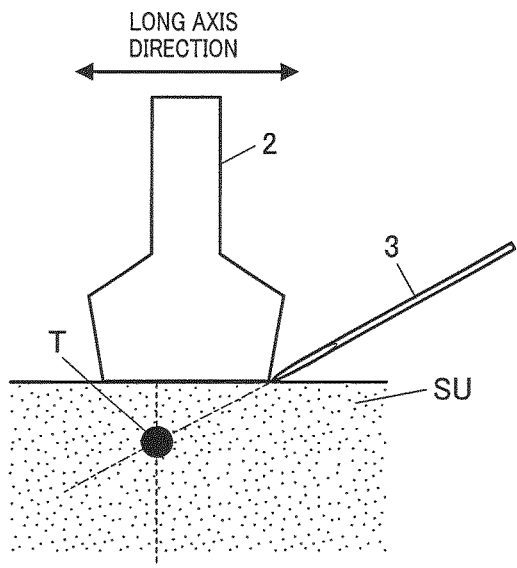
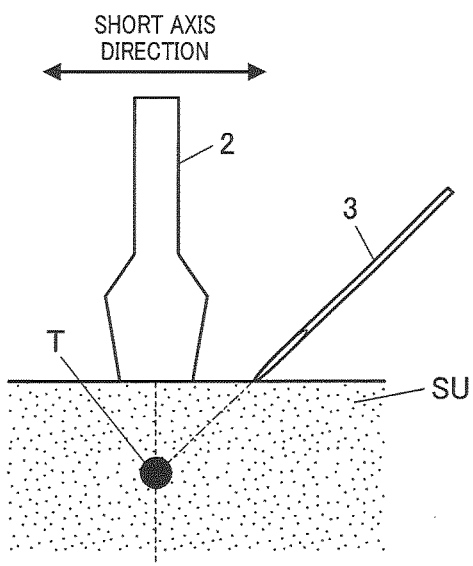
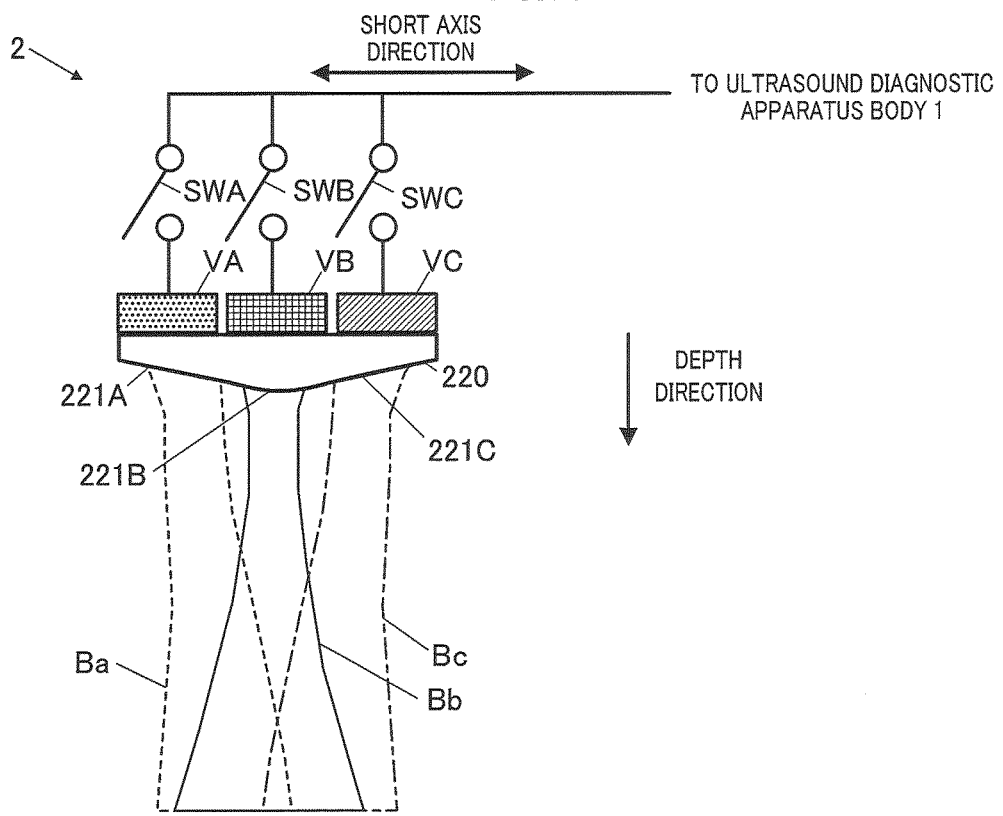

⊗ SHORT AXIS DIRECTION

⊙ SHORT AXIS DIRECTION

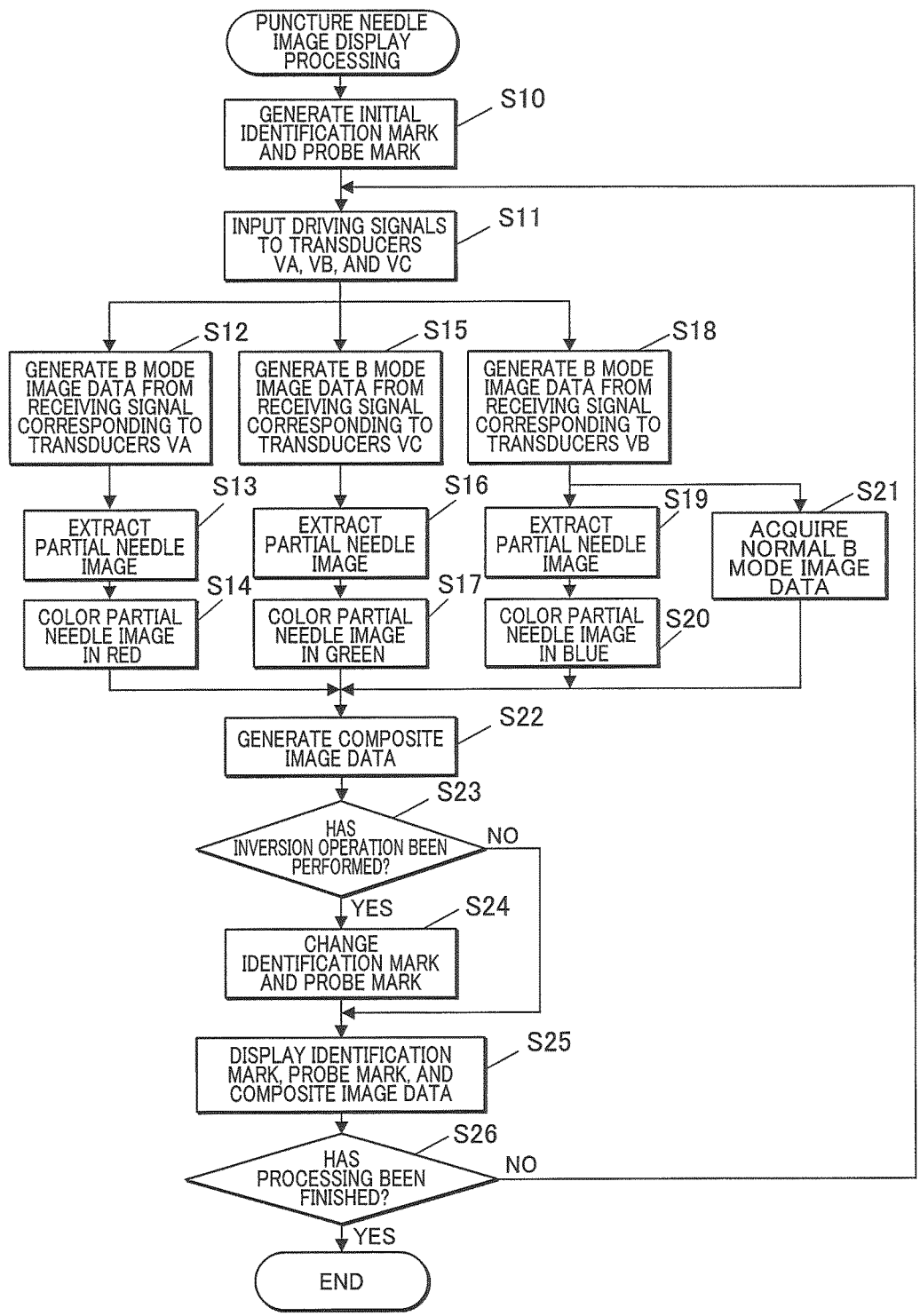

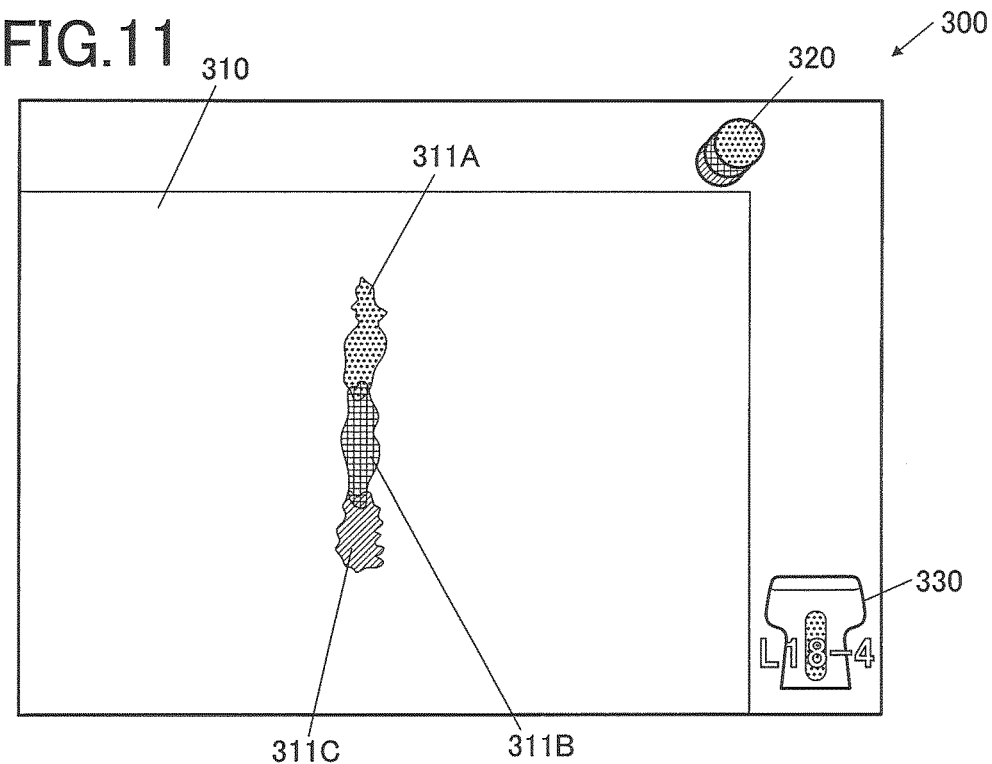
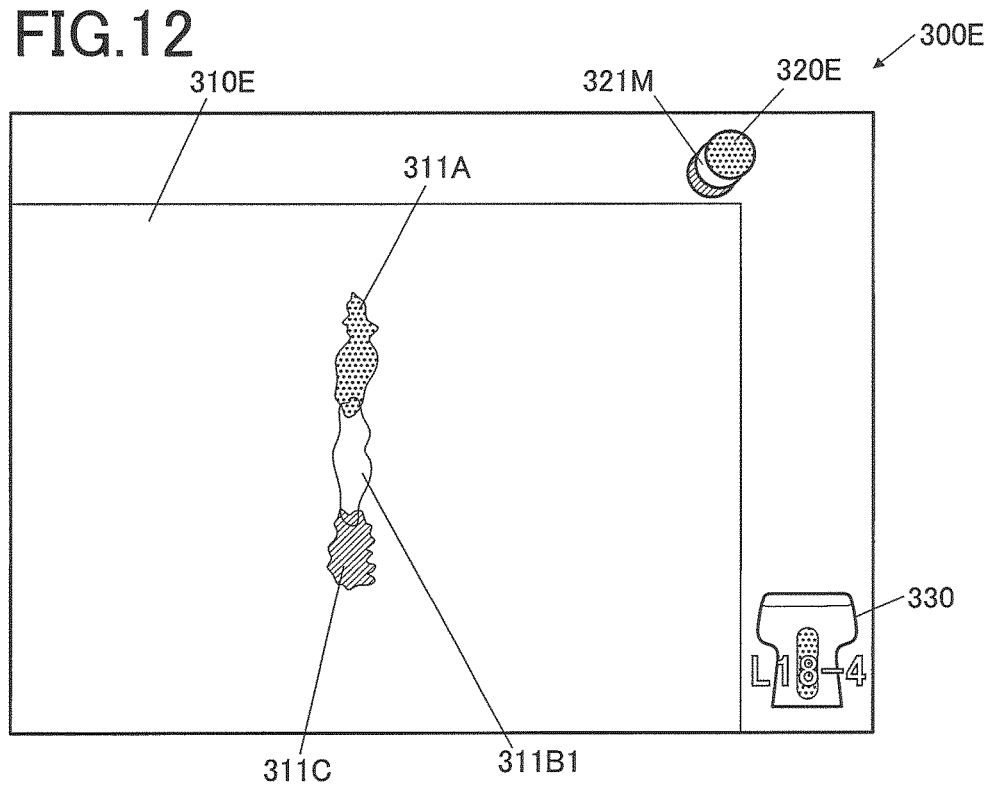

⊗ SHORT AXIS DIRECTION

⊙ SHORT AXIS DIRECTION

ULTRASOUND DIAGNOSTIC APPARATUS

CROSS-REFERENCE TO RELATED APPLICATION

The present application claims priority under 35 U.S.C. § 119 to Japanese Patent Application No. 2018-004649, filed on Jan. 16, 2018, the entirety of which is hereby incorporated by reference herein and forms a part of the specification.

BACKGROUND

Technological Field

The present invention relates to an ultrasound diagnostic apparatus.

Description of the Related Art

Conventionally, an ultrasound diagnostic apparatus has been known which irradiates ultrasound into a subject, receives its reflected ultrasound, and performs predetermined signal data processing to generate an ultrasound image of an internal structure of the subject. The ultrasound diagnostic apparatus has been widely used for various applications such as inspection for medical purposes, medical treatment, and inspection of the inside of architectural construction.

The ultrasound diagnostic apparatus has been used to not only display an ultrasound image but also insert, in collecting a sample of a specific site (target) within a subject, discharging water or the like, or injecting or placing a medical agent, a marker, or the like into the specific site, a puncture needle used for the injection and the placement into a position of the target while visually recognizing the puncture needle and the position of the target. Treatment for the target within the subject can be quickly, reliably, and easily performed by using the ultrasound image.

As the ultrasound diagnostic apparatus, an ultrasound diagnostic apparatus, in which transducers which transmit and receive ultrasound are arranged in a one-dimensional or two-dimensional matrix shape and which performs image pickup while subjecting a position and a direction in which the ultrasound is transmitted and received to scanning (electronic scanning in particular) in a predetermined arrangement direction, has been frequently used. The puncture needle is positioned in a range in which image pickup can be consecutively performed in a time period elapsed until the puncture needle reaches a target after being inserted into a subject when inserted along a direction of the scanning (a lateral direction) by an operation of an operator such as a doctor. Although the puncture needle has been previously attached to an attachment fixedly connected to an ultrasound probe called a puncturing guide and inserted, the operator may frequently insert the puncture needle freehand at present.

Therefore, the puncture needle may not necessarily be accurately oriented in a first insertion direction or may be bent depending on an internal state and a structure of the subject and a shape of a distal end of the puncture needle, for example. As a result, a case has occurred where the distal end of the puncture needle deviates from a range in which image pickup can be performed in an elevation direction perpendicular to the scanning direction so that image pickup is not performed. Even when a cross-sectional image is simply obtained without using puncture, if an operator is unaccustomed, appropriate change cannot be performed even when an image pickup range in the elevation direction is finely adjusted by changing a posture of the ultrasound probe. Thus, it may take a time and a labor to obtain a desired image.

Therefore, an ultrasound diagnostic apparatus has been known which includes, in an ultrasound probe in which a plurality of transducers are two-dimensionally arranged, a deflection control circuit including a delay circuit and a deflection changeover switch which input and output transmission and receiving signals to and from each of the plurality of transducers in a short axis direction (elevation direction) perpendicular to a long axis direction (scanning direction) in the arrangement, shifts a timing of the transmission signal and delays the receiving signal and adds the transmission signal and the receiving signal using the deflection control circuit, to deflect an ultrasound beam in the short axis direction, and displays a puncture needle which has shifted in the short axis direction from a target (see Japanese Patent Laid-Open No. 2000-139926).

An ultrasound diagnostic apparatus has been known which deflects, in an ultrasound probe in which a plurality of transducers are two-dimensionally arranged and are respectively entirely covered with acoustic lenses having substantially identical curvatures, an ultrasound beam in a short axis direction and displays a puncture needle which has shifted in the short axis direction from a target when the plurality of transducers are divided into transducer groups in the short axis direction and some of the transducer groups are used for transmission and receiving (see Japanese Patent Laid-Open No. 2016-47191).

An ultrasound probe has been known which can determine a grasping direction of an operator by having a front mark provided on one of its side surfaces (see Japanese Patent Laid-Open No. 2006-326204). In addition, a probe for ultrasound diagnostic apparatus (an ultrasound probe) has been known, the top, the bottom, the right, and the left of which can be identified by an operator by having a non-slip portion on one of its side surfaces (see Japanese Patent Laid-Open No. 9-313491).

However, in respective techniques disclosed in Japanese Patent Laid-Open No. 2000-139926 and Japanese Patent Laid-Open No. 2016-47191, when one tomographic image is displayed as an ultrasound image, an operator can visually recognize a puncture needle which has deviated in a short axis direction but cannot recognize whether the direction in which the puncture needle has deviated is on the front side or the back side of the tomographic image. In respective techniques disclosed in Japanese Patent Laid-Open No. 2006-326204 and Japanese Patent Laid-Open No. 9-313491, an operator can recognize a gripping direction of an ultrasound probe but cannot easily recognize a relationship between a displayed tomographic image and the ultrasound probe.

SUMMARY

The present invention is directed to easily recognizing a position in a depth direction of a recognition object such as a puncture needle.

To achieve at least one of the abovementioned objects, according to a first aspect of the present invention, an ultrasound diagnostic apparatus reflecting one aspect of the present invention includes:

an ultrasound probe including a plurality of transducers which are arranged in a plurality columns in a long axis direction arranged in a short axis direction and transmit and receive ultrasound and a switching element which switches on and off of input of a driving signal to the transducers in each of the columns and output of a receiving signal;

a transmitter which outputs the driving signal to the transducers in each of the columns in the ultrasound probe via the switching by the switching element;

a receiver which acquires the receiving signal corresponding to the transducers in each of the columns from the ultrasound probe via the switching by the switching element; and a hardware processor which generates ultrasound image data corresponding to each of the columns from the receiving signal corresponding to the column, makes partial images of a recognition object in the plurality of ultrasound image data respectively have representations separately identifiable in each of the columns, synthesizes the plurality of ultrasound image data respectively including the partial images to generate composite image data, generates first identification information indicating to which position in a depth direction of a composite image represented by the composite image data each of the representations of the partial images in the composite image data corresponds, and displays the first identification information and the composite image data, which are generated, on a display.

According to a second aspect of the present invention, an ultrasound diagnostic apparatus reflecting one aspect of the present invention includes:

an ultrasound probe including a plurality of transducers which are arranged in a plurality columns in a long axis direction arranged in a short axis direction and transmit and receive ultrasound and a switching element which switches on and off of input of a driving signal to the transducers in each of the columns and output of a receiving signal;

a transmitter which outputs the driving signal to the transducers in each of the columns in the ultrasound probe via the switching by the switching element;

a receiver which acquires the receiving signal corresponding to the transducers in each of the columns from the ultrasound probe via the switching by the switching element; and a hardware processor which generates ultrasound image data corresponding to each of the columns from the receiving signal corresponding to the column, makes partial images of a recognition object in the plurality of ultrasound image data respectively have representations separately identifiable in each of the columns, synthesizes the plurality of ultrasound image data respectively including the partial images to generate composite image data, and displays the generated composite image data on a display, in which the ultrasound probe includes an identifier which represents the representation of the partial image corresponding to a position in the short axis direction.

According to a third aspect of the present invention, an ultrasound diagnostic apparatus reflecting one aspect of the present invention includes:

an ultrasound probe including a plurality of transducers which are arranged in at least one of columns in a long axis direction arranged in a short axis direction and transmit and receive ultrasound and an identifier which represents a front and a back in the short axis direction, a transmitter which outputs driving signals to the transducers in the ultrasound probe;

a receiver which acquires receiving signals from the transducers in the ultrasound probe; and a hardware processor which generates ultrasound image data from the receiving signal, generates third identification information representing a representation of at least one of the front and the back of the ultrasound probe corresponding to a front and a back of the ultrasound image data, and displays the third identification information and the ultrasound image data, which are generated, on a display.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 4A is a schematic view illustrating a parallel method in ultrasonically guided puncture;

FIG. 4B is a schematic view illustrating a crossing method in ultrasonically guided puncture;

FIG. 5 is a diagram illustrating a schematic configuration in a short axis direction of the ultrasound probe;

FIG. 8 is a flowchart illustrating puncture needle image display processing;

FIG. 11 is a diagram illustrating an ultrasound diagnostic screen according to the embodiment;

FIG. 12 is a diagram illustrating an ultrasound diagnostic screen according to a first modification;

DETAILED DESCRIPTION OF EMBODIMENTS

Hereinafter, one or more embodiments of the present invention will be described with reference to the drawings. However, the scope of the invention is not limited to the disclosed embodiments.

An embodiment and first and second modifications according to the present invention will be sequentially described in detail with reference to the accompanying drawings.

Embodiment

Figure 1:
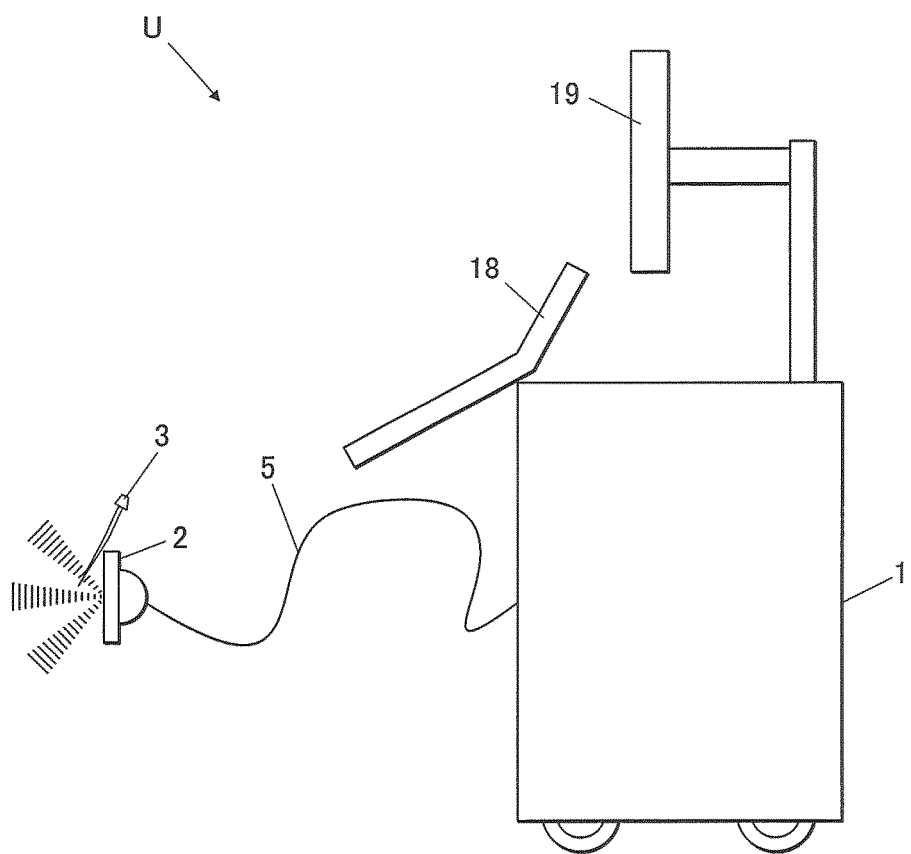
FIG. 1 is an overall view of an ultrasound diagnostic apparatus according to an embodiment of the present invention.
Figure 2:
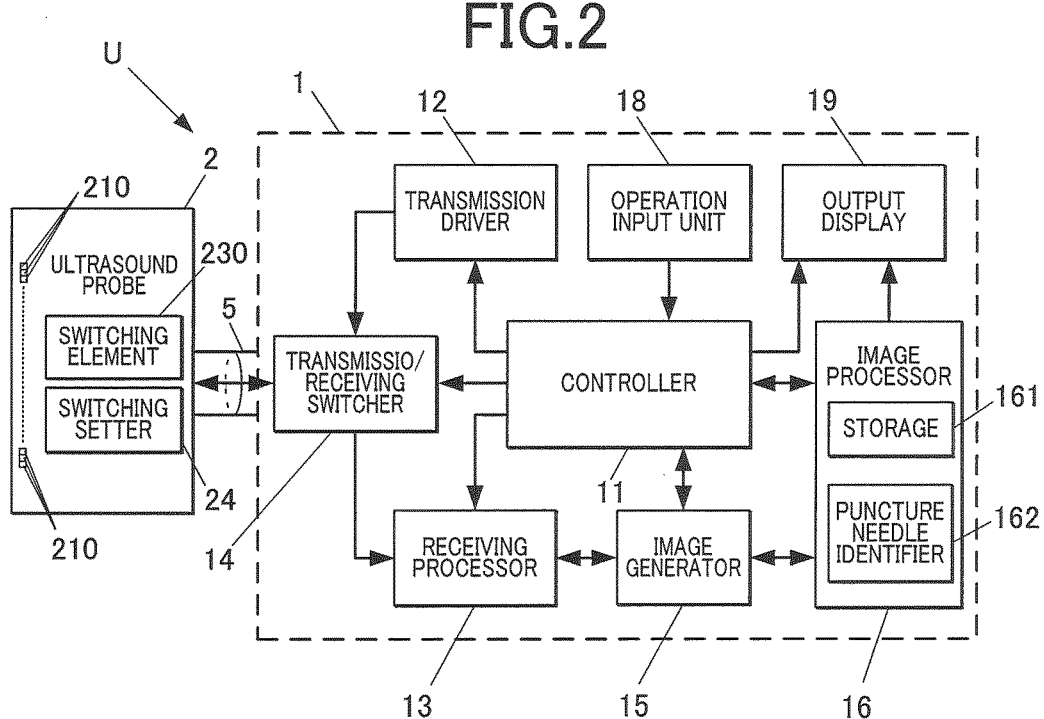
FIG. 2 is a block diagram illustrating an internal configuration of the ultrasound diagnostic apparatus.

An embodiment of the present invention will be described below with reference to FIG. 1 to FIG. 11. First, an entire apparatus configuration of an ultrasound diagnostic apparatus U according to the present embodiment will be described with reference to FIG. 1 and FIG. 2. FIG. 1 is an overall view of the ultrasound diagnostic apparatus U according to the present embodiment. FIG. 2 is a block diagram illustrating an internal configuration of the ultrasound diagnostic apparatus U.

As illustrated in FIG. 1, the ultrasound diagnostic apparatus U includes an ultrasound diagnostic apparatus body 1, an ultrasound probe 2 connected to the ultrasound diagnostic apparatus body 1 via a cable 5, and a puncture needle 3 which is a treatment instrument as a recognition object.

The puncture needle 3 has a hollow long needle shape, and is inserted into a subject at an angle determined freehand by an operator such as a doctor. The puncture needle 3 can be converted into a puncture needle having an appropriate thickness, length, and distal end shape depending on a site (target) to be collected of a subject such as a patient or the type or the amount of a medical agent or the like to be injected. In the ultrasound diagnostic apparatus U, an attachment section as an attachment which guides the puncture needle 3 in a puncture direction and a guide section which is fixedly provided in the ultrasound probe 2 and guides the puncture needle 3 in the puncture direction may be provided.

The ultrasound diagnostic apparatus body 1 is provided with an operation input unit 18 as an operation unit and an output display 19 as a display. As illustrated in FIG. 2, the ultrasound diagnostic apparatus body 1 includes a controller 11 as an identification information generator and a display controller, a transmission driver 12 as a transmitter, a receiving processor 13 as a receiver, a transmission/receiving switcher 14, an image generator 15, and an image processor 16, for example, in addition to the operation input unit 18 and the output display 19. The controller 11 outputs a driving signal to the ultrasound probe 2 to output ultrasound based on an input operation from outside to an input device such as a keyboard or a mouse in the operation input unit 18, acquires a receiving signal relating to ultrasound receiving from the ultrasound probe 2 to perform various types of processing, and displays a result or the like on a display screen or the like of the output display 19, as needed.

The controller 11 includes a CPU (central processing unit), an HDD (hard disk drive), and a RAM (random access memory), for example. The CPU reads out various types of programs stored in the HDD and loads the read programs into the RAM, to integrally control respective operations of the units in the ultrasound diagnostic apparatus U according to the programs. The HDD stores a control program and various types of processing programs for causing the ultrasound diagnostic apparatus U to operate and various types of setting data, for example. The HDD particularly stores a puncture needle image display program for performing puncture needle image display processing, described below. The programs and the setting data may be stored such that reading and writing are updatable in an auxiliary storage device using a nonvolatile memory such as a flash memory including an SSD (solid state drive), for example, in addition to the HDD. The RAM is a volatile memory such as an SRAM (Static random-access memory) or a DRAM (Dynamic random-access memory), and provides a work memory space to the CPU and stores temporary data.

The transmission driver 12 outputs a driving signal to be fed to the ultrasound probe 2 in response to a control signal inputted from the controller 11, and transmits ultrasound to the ultrasound probe 2. The transmission driver 12 includes a clock generation circuit, a pulse width setter, a pulse generation circuit, and a delay circuit, for example. The clock generation circuit is a circuit which generates clock signals to determine a transmission timing and a transmission frequency of a pulse signal. The pulse width setter sets a waveform (shape), a voltage amplitude, and a pulse width of a transmission pulse to be outputted from the pulse generation circuit. The pulse generation circuit generates a transmission pulse as a driving signal based on the setting by the pulse width setter, and outputs the generated transmission pulse to wiring paths which differ for each of transducers 210 in the ultrasound probe 2. The delay circuit counts the clock signals outputted from the clock generation circuit, and causes the pulse generation circuit to generate a transmission pulse and output the generated transmission pulse to each of the wiring paths when a set delay time period elapses.

The receiving processor 13 is a circuit which acquires the receiving signal inputted from the ultrasound probe 2 under the control of the controller 11. The receiving processor 13 includes an amplifier, an A/D (analog to digital) conversion circuit, and a phase-adjustment and addition circuit, for example. The amplifier is a circuit which amplifies receiving signals corresponding to ultrasound received by the transducers 210 in the ultrasound probe 2, respectively, at predetermined amplification factors previously set. The A/D conversion circuit is a circuit which respectively converts the amplified receiving signals into digital data at a predetermined sampling frequency. The phase-adjustment and addition circuit is a circuit which gives the receiving signals, which have been subjected to A/D conversion, delay time periods for wiring paths corresponding to the transducers 210 to adjust their respective time phases and add the time phases to generate sound ray data.

The transmission/receiving switcher 14 performs a switching operation for transmitting a driving signal to the transducers 210 from the transmission driver 12 when emitting (transmitting) ultrasound from the transducers 210 while outputting a receiving signal to the receiving processor 13 when acquiring a signal relating to the ultrasound emitted by the transducers 210 under the control of the controller 11.

The image generator 15 generates a diagnostic image based on ultrasound receiving data. The image generator 15 subjects the sound ray data inputted from the receiving processor 13 to detection (envelope detection) to acquire a signal, and performs logarithmic amplification, filtering (e.g., low-pass transmission or smoothing), and enhancement processing, for example, as needed. The image generator 15 generates as one of diagnostic images frame image data relating to B (Brightness) mode display as a tomographic image representing a two-dimensional structure within a cross section including a transmission direction of a luminance signal corresponding to the intensity of the signal (a depth direction of the subject) and a scanning direction (a lateral direction and a long axis direction in a two-dimensional arrangement of the transducers 210) of the ultrasound transmitted by the ultrasound probe 2. At this time, the image generator 15 can perform dynamic range adjustment and gamma correction relating to display, for example. The image generator 15 can be configured to include a dedicated CPU and RAM used for image generation. Alternatively, in the image generator 15, a dedicated hardware configuration relating to image generation may be formed on a substrate (e.g., an ASIC (application-specific integrated circuit)) or formed by an FPGA (field programmable gate array)). Alternatively, the image generator 15 may have a configuration in which the CPU and the RAM in the controller 11 perform processing relating to image generation.

The image processor 16 includes a storage 161 and a puncture needle identifier 162, for example. The storage 161 stores diagnostic image data (frame image data), which is used for real time display or display conforming thereto upon being processed by the image generator 15, corresponding to a predetermined number of latest frames frame by frame. The storage 161 is, for example, a volatile memory such as a DRAM (dynamic random access memory). Alternatively, the storage 161 may be various types of high-speed rewritable nonvolatile memories. The diagnostic image data stored in the storage 161 is read out under the control of the controller 11, is transmitted to the output display 19, and is outputted to outside the ultrasound diagnostic apparatus U via a communicator (not illustrated). At this time, if a display system of the output display 19 is a television system, a DSC (digital scan converter) may be provided between the storage 161 and the output display 19 so that the diagnostic image data is outputted after a scanning format has been converted.

The puncture needle identifier 162 generates image data for identifying a position of the puncture needle 3, performs appropriate processing for the image data to extract and identify a partial needle image at a position including a distal end of the puncture needle 3 and colors the extracted partial needle image of the puncture needle 3. The puncture needle identifier 162 may share a CPU and a RAM in the image processor 16, or may include a dedicated CPU and RAM. Alternatively, the puncture needle identifier 162 may perform various types of processing using the CPU and the RAM in the controller 11. The puncture needle identifier 162 can store and hold distal end position information of the identified puncture needle 3 as a history.

Examples of a method for identifying a position of the puncture needle 3 include a method for finding from ultrasound image data in a plurality of frames a difference and a correlation among the frames to generate movement evaluation information representing evaluation of movement, calculating a movement speed of a distal end of the puncture needle, and detecting a position of the distal end of the puncture needle from the movement speed of the distal end of the puncture needle and the movement evaluation information, to identify a position of the puncture needle including the distal end, as described in Japanese Patent No. 6123458. A method for estimating a subsequent position of a distal end of a puncture needle 3 based on a movement history of the distal end, and detecting the distal end based on the estimated position, to identify a position of the puncture needle including the distal end may be used. A method for an operator selecting one of contour candidates first obtained by performing contour detection using an input operation to the operation input unit 18 and detecting a contour similar to the selected contour candidate, to detect a position of the puncture needle based on the abovementioned estimated position may be used.

The operation input unit 18 includes a push button switch, a keyboard, a mouse, or a trackball or their combinations, and converts a user's input operation into an operation signal and inputs the operation signal to the ultrasound diagnostic apparatus body 1.

The output display 19 includes a display screen using any one of various display systems such as an LCD (liquid crystal display), an organic EL (electro-luminescent) display, an organic EL display, a plasma display, and a CRT (cathode ray tube) display and a driver for the display screen. The output display 19 generates a control signal outputted from the CPU 11 and a driving signal of a display screen (each display pixel) according to the image data generated by the image processor 16, and displays measurement data based on a menu, a status, and a received ultrasound relating to ultrasound diagnosis on the display screen. The output display 19 may be configured to display the presence or absence of turn-on of power by separately including an LED (light emitting diode) lamp, for example.

The operation input unit 18 and the output display 19 may be provided to be integrated with a housing of the ultrasound diagnostic apparatus body 1, or may be attached to the outside via an RGB (Red, Green and Blue) cable, a USB (universal serial bus) cable, an HDMI (high-definition multimedia interface) cable (registered trademark: HDMI), or the like. If the ultrasound diagnostic apparatus body 1 is provided with an operation input terminal and a display output terminal, the operation input unit 18 and the output display 19 may be used by respectively connecting peripheral devices for operation and for display to the terminals.

The ultrasound probe 2 functions as an acoustic sensor which transmits ultrasound (approximately 1 to 30 MHz) and emits the transmitted ultrasound to a subject such as a living body while receiving a reflection wave (echo) reflected on the subject among the emitted ultrasound and converting the received reflection wave into an electrical signal.

The ultrasound probe 2 includes a plurality of transducers 210 which transmit and receive ultrasound, a plurality of switching elements 230 respectively corresponding to the transducers 210, and a switching setter 24. Although the ultrasound probe 2 is here explained as an ultrasound probe which emits the ultrasound into the subject from the outside (a body surface) and receives its reflection wave, examples of the ultrasound probe 2 include an ultrasound probe having a size and a shape used by being inserted into a digestive tube or a blood vessel or a body cavity, for example. The operator performs ultrasound diagnosis by making a transmission/receiving surface of the ultrasound in the ultrasound probe 2, i.e., a surface in a direction in which the ultrasound is emitted from the transducers 210 contact the subject at predetermined pressure to operate the ultrasound diagnostic apparatus U.

The number of transducers of the transducers 210 can be optionally set. Although an electronic scan probe using a linear scanning method is adopted for the ultrasound probe 2 in the present embodiment, either one of an electronic scanning method and a mechanical scanning method may be adopted, or any one of a linear scanning method, a sector scanning method, and a convex scanning method can also be adopted.

The transducers 210 are a plurality of transducers each including a piezoelectric element including a piezoelectric body and electrodes provided at both ends where a charge appears by deformation (expansion and contraction) of the piezoelectric body.

When a voltage pulse as a driving signal is supplied to each of the plurality of transducers 210, the piezoelectric body in the transducer to which the voltage pulse has been supplied deforms (expands and contracts) in response to an electric field occurring in the piezoelectric body so that ultrasound is transmitted. The transmitted ultrasound is emitted in a position and a direction corresponding to a position and a direction of the transducers 210 included in each of a predetermined number of transducer columns to which the voltage pulse has been supplied, a focusing direction of the transmitted ultrasound, and the magnitude of a shift in timing (a delay). When ultrasound (a reflection wave on the subject) in a predetermined frequency band is incident in one of the transducers 210, the thickness of the piezoelectric body varies (vibrates) with sound pressure of the ultrasound so that a charge corresponding to an amount of the variation occurs. The charge is converted into an electrical signal corresponding to an amount of the charge, and the electrical signal is outputted as a receiving signal.

The switching setter 24 stores a setting of a transmission/receiving sequence of the transducers 210 for performing transmission/receiving of ultrasound in a short axis direction (elevation direction) in the two-dimensional arrangement of the transducers 210, and performs an operation for switching on and off of the switching element 230 corresponding to each of the transducers 210 in response to the setting. The transmission/receiving sequence of the transducers 210 will be described below.

The cable 5 includes a connector (not illustrated) to the ultrasound diagnostic apparatus body 1 and a connector (not illustrated) to the ultrasound probe 2, respectively, at both its ends, and the ultrasound probe 2 is configured to be detachably attached to the ultrasound diagnostic apparatus body 1 via the cable 5. The cable 5 may be formed integrally with the ultrasound probe 2.

Figure 3:
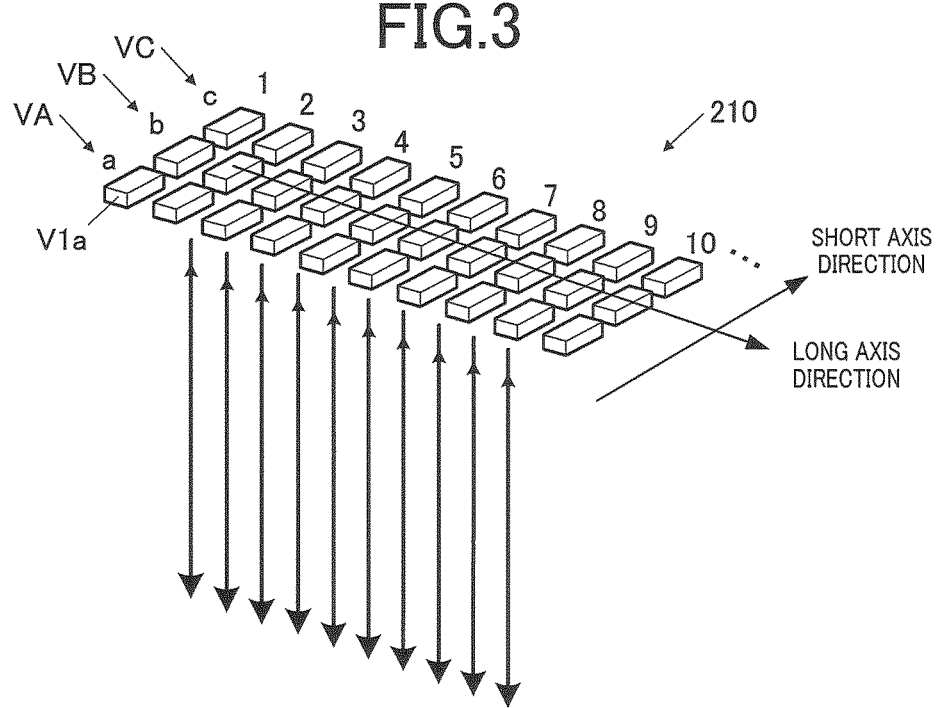
FIG. 3 is a diagram illustrating an example of an arrangement of transducers in an ultrasound probe.
Figure 6A:
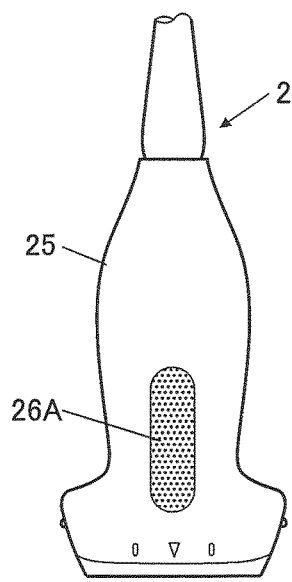
FIG. 6A is a plan view of a front surface of the ultrasound probe according to the embodiment.
Figure 6B:
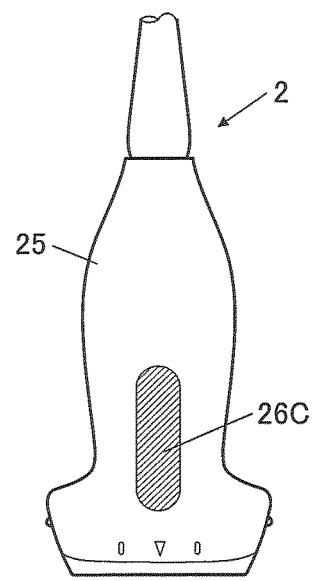
FIG. 6B is a plan view of a back surface of the ultrasound probe according to the embodiment.
Figure 7:
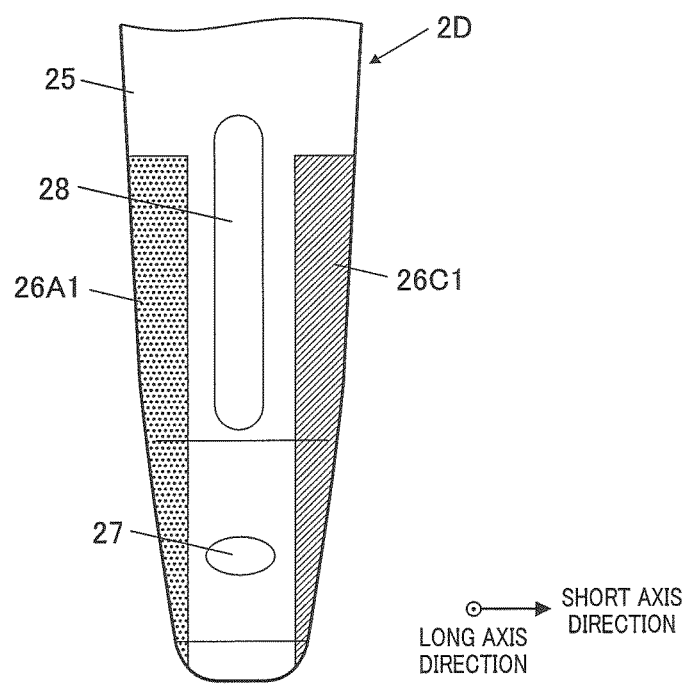
FIG. 7 is a side view of an ultrasound probe having an example of a different outer shape.

A more detailed configuration and operation of the ultrasound probe 2 will be described with reference to FIG. 3 to FIG. 7. FIG. 3 is a diagram illustrating an example of an arrangement of the transducers 210 in the ultrasound probe 2. FIG. 4A is a schematic view illustrating a parallel method in ultrasonically guided puncture. FIG. 4B is a schematic view illustrating a crossing method in ultrasonically guided puncture. FIG. 5 is a diagram illustrating a schematic configuration in a short axis direction of the ultrasound probe 2. FIG. 6A is a plan view of a front surface of the ultrasound probe 2. FIG. 6B is a plan view of a back surface of the ultrasound probe 2. FIG. 7 is a side view of an ultrasound probe 2D having an example of a different outer shape.

As illustrated in FIG. 3, in the ultrasound diagnostic apparatus U, the transducers 210 are a plurality of transducers arranged in a matrix shape within a two-dimensional plane (which may not be a flat surface) defined by a predetermined lateral direction (scanning direction) and an elevation direction perpendicular to the lateral direction. Generally, the number of arrangements of the transducers 210 in the lateral direction is larger than the number of arrangements of the transducers 210 in the elevation direction, and the lateral direction and the elevation direction are respectively a long axis direction and a short axis direction. The transducers 210 include transducer groups in three columns (columns a, b, and c) in the short axis direction, and transducers in a plurality of stages (stages 1, 2, . . . ) are arranged in the long axis direction in each of the columns. The transducer group in the column a is conveniently represented as transducers VA. Similarly, the transducer groups in the columns b and c are conveniently represented, respectively, as transducers VB and VC. The one transducer in the stage x and the column y is represented as a transducer Vxy.

If a normal B mode (tomographic) image is generated, ultrasound is transmitted and received while the transducers to be driven are sequentially shifted in the long axis direction using the transducers VB in the column b.

A parallel method and a crossing method will be described as a puncture method for the puncture needle 3 in ultrasonically guided puncture with reference to FIG. 4A and FIG. 4B.

As illustrated in FIG. 4A, the parallel method is a method for inserting the puncture needle 3 parallel to the long axis direction into a target T, for example, acquiring tissues by puncturing the subject SU. As illustrated in FIG. 4B, the crossing method is a method for inserting the puncture needle 3 in a direction perpendicular to the long axis direction into the target T in the subject SU. The parallel method and the crossing method are differently used depending on uses. Although it may be determined which of the methods is to be used depending on a site to be punctured and a purpose of puncture, the method may be selected by an empirical value of an operator.

In the parallel method, if the puncture needle is inserted, the puncture needle is inserted into the subject SU from a long axis end of the ultrasound probe, and is inserted toward a depth within a tomographic plane formed by the puncture needle in the long axis direction as the one column corresponding to the transducers VB. If the puncture needle 3 deviates in the short axis direction from the inside of the tomographic surface in this case, the puncture needle 3 is not depicted in a conventional ultrasound diagnostic apparatus.

In the crossing method, the puncture needle 3 is obliquely inserted into the subject SU from the short axis side of the ultrasound probe, and is inserted into the target T directly below the ultrasound probe. When a general ultrasound probe is used in a conventional crossing method, even if a puncture needle 3, which has been inserted into a body surface, reaches a significant depth, the puncture needle 3 is not displayed on an ultrasound image, and an image of the puncture needle first appears in the ultrasound image immediately near a target T. Therefore, it is difficult to know whether the inserted puncture needle 3 advances in a correct direction.

In the present embodiment, the puncture needle 3 is captured in a wide region in both the parallel method and the crossing method. Accordingly, a frame of an ultrasound image by the transducers VA and a frame of an ultrasound image by the transducers VC are obtained in addition to a frame of the ultrasound image by the transducers VB at the same time.

As illustrated in FIG. 5, the ultrasound probe 2 includes an acoustic lens 220, transducers VA, VB, and VC, and switches SWA, SEB, and SWC in a switching element 230 respectively corresponding to the transducers VA, VB, and VC in the short axis direction viewed from the long axis end. Illustration of an acoustic matching layer arranged between the acoustic lens 220 and the transducers VA, VB, and VC and a backing material arranged on the opposite side to the ultrasound emission direction of the transducers VA, VB, and VC, for example, is omitted.

The acoustic lens 220 is a lens having an aspherical shape which makes ultrasound beams (transmission ultrasound) respectively emitted from the transducers VA, VB, and VC focus. The acoustic lens 220 includes a lens portion 221A through which an ultrasound beam Ba emitted from the transducers VA passes, a lens portion 221B through which an ultrasound beam Bb emitted from the transducers VB passes, and a lens 221C through which an ultrasound beam Bc emitted from the transducers VC passes.

The switch SWA is a switch which can independently turn on and off input of a driving signal to each of the transducers in the transducers VA from the transmission/receiving switcher 14 and output of a receiving signal via the switching setter 24 and the cable 5. The switch SWB is a switch which can independently turn on and off input of a driving signal to each of the transducers in the transducers VB from the transmission/receiving switcher 14 and output of a receiving signal via the switching setter 24 and the cable 5. The switch SWC is a switch which can independently turned on and off input of a driving signal to each of the transducers in the transducers VC from the transmission/receiving switcher 14 and output of a receiving signal via the switching setter 24 and the cable 5.

In the present embodiment, the transducers VA, VB, and VC are arranged such that the ultrasound beams Ba, Bb, and Bc do not substantially overlap one another to a certain depth and a gap is not formed among the ultrasound beams Ba, Bb, and Bc.

A short axis width of the transducers VB has a width wide enough to withstand normal ultrasound scanning. The lens portion 221B in the acoustic lens 220, which covers the transducers VB, has a beam formation capability usable for normal ultrasound scanning. Respective short axis widths of the transducers VA and VC each have a width wide enough to sufficiently obtain a reflection wave (echo) of the inserted puncture needle 3, although the widths may be narrower than that of the transducers VB. Although the lens portions 221A and 221C in the acoustic lens 220, which respectively cover the transducers VA and VC, each desirably have such an aspherical shape that its radius of curvature becomes larger than that of the lens portion 221B, an obliquely flat shape can also be used. Although a shape, which is not oblique but is flat, is not entirely disapproved, the shape may be desirably oblique when fusion with the ultrasound beam Bb by the transducers VB, described below, is considered. A lens shape of the lens portion 221B may be an aspherical shape in an advantage that the lens portion 221B can be smoothly connected to the lens portions 221A and 221C if an inconvenience (e.g., a side robe becomes large) does not arise in normal ultrasound scanning.

To accurately capture a position of the puncture needle 3, positions respectively occupied by the ultrasound beams Ba, Bb, and Bc transmitted and received by the transducers VA, VB, and VC are desirably exclusive. The positions occupied by the ultrasound beams Ba, Bb, and Bc are easily determined by being exclusive because the reflection wave (echo) from the puncture needle 3 is included in only a reflection wave from any one of the transducers VA, VB, and VC.

However, directivity of the ultrasound beam has a shape having a smooth skirt. Thus, the ultrasound beams Ba, Bb, and Bc overlap one another in the skirt. Accordingly, the ultrasound beams Ba, Bb, and Bc are not completely exclusive, as illustrated in FIG. 5. In a graph of the directivity of the ultrasound beams Ba, Bb, and Bc at a certain depth for an azimuth angle in the short axis direction, to facilitate determination which of the ultrasound beams includes a reflection wave of the puncture needle 3, it has been experimentally apparent that a point at which the adjacent ultrasound beams reach the same level is preferably −6 [dB] to −12 [dB] from a peak of the transmitted or received ultrasound beam. Correction for making the respective heights of peaks of the directivity of the ultrasound beams by the transducers VA and VC equal to the height of the directivity of the ultrasound beam by the transducers VB may be performed. If the transducers greatly differ in sensitivity, a needle position can thus be accurately captured. Since a difference in sensitivity among the transducers occurs depending on a depth, correction may be performed if the difference is large.

An appropriate shape of the acoustic lens 220 in the present embodiment will be described below. First, the ultrasound beam by the transducers VB thins from the vicinity of the transducers VB toward a focus. That is, the ultrasound beams by the transducers VA and VC need to fill the right and the left of the ultrasound beam, which thins, by the transducers VB (have directivity). When in directivity between the ultrasound beam by the transducers VA and the ultrasound beam by the transducers VB, or directivity between the ultrasound beam by the transducers VC and the ultrasound beam by the transducers VB, there is a gap (strictly, a zone where respective sensitivities of both the ultrasound beams are low), the puncture needle 3 becomes difficult to be captured when positioned in the gap. Therefore, the acoustic lens 220 desirably has such a lens shape that the ultrasound beam by the transducers VA and the ultrasound beam by the transducers VC deflect inward.

However, when the respective ultrasound beams by the transducers VA and VC respectively focus at shallow positions close to the transducers VA and VC, the inserted puncture needle 3 does not easily enter the ultrasound beams, i.e., cannot be captured in the puncture using the crossing method. When considered from the foregoing, the respective ultrasound beams by the transducers VA and VC desirably focus at a deep position or does not focus, although they deflect.

If the acoustic lens having such a lens shape that the ultrasound beam by the transducers VA and the ultrasound beam by the transducers VC deflect inward is used, as a depth increases, the respective ultrasound beams by the transducers VA and VC overlap the ultrasound beam at the center by the transducers VB so that the position of the puncture needle 3 cannot be determined. Therefore, the respective ultrasound beams by the transducers VA, VB, and VC are desirably separated from one another such that a deflection angle is not made too large and the position of the puncture needle 3 can be determined up to a depth at which there is no clinical problem.

To which depth the ultrasound beams are separated from one another depends on a diagnostic site. However, the ultrasound beams can be desirably separated from one another up to 25 to 30 [mm] when a high-frequency linear probe is used as the ultrasound probe 2, for example. Examples of a shape of the acoustic lens matching the abovementioned condition include a lens shape of the acoustic lens 220 having the aspherical shape as illustrated in FIG. 5. The acoustic lens 220 has a shape in which a curvature is strong (a radius of curvature is small) in the lens portion 221B corresponding to the transducers VB and a curvature is weak (a radius of curvature is large) in the lens portions 221A and 221C corresponding to the transducers VA and VC.

Although the acoustic lens 220 is used, as illustrated in FIG. 5, in the parallel method, if the switch SWB is turned on and the switches SWA and SWC are turned off, ultrasound is transmitted and received using the transducers VB. However, for an operation in this case, the transmission and receiving of the ultrasound do not differ from transmission and receiving of ultrasound by a conventional ultrasound diagnostic apparatus.

If the switch SWA is turned on and the switches SWB and SWC are turned off, ultrasound is transmitted and received using the transducers VA. However, the lens portion 221A corresponding to the transducers VA has a substantially oblique aspherical shape. Accordingly, a transmission/receiving beam of the ultrasound deflects toward the center of the transducers, and an intersection between the transmission/receiving beam and a center line is at a position farther than a focusing point of the lens portion 221B corresponding to the transducers VB. If the lens portions 221A and 221C are respectively provided with curvatures, the curvatures are each desirably such a curvature that the transmission/receiving beam focuses in the vicinity of the intersection. The transmission/receiving beams of the ultrasound respectively formed by the acoustic lens 220 and the transducers VA, VB, and VC do not overlap one another to a desired depth, and a gap (a dead angle on sensing) is not formed among the transmission/receiving beams. In the present embodiment, not only a tomographic image using the transducers VB but also tomographic images respectively using the transducers VA and VC are formed in the parallel method. Accordingly, a puncture needle, which has deviated from a surface of the tomographic image using the transducers VB, can be captured.

For the crossing method, in the ultrasound probe 2 according to the present embodiment, the target T in the subject SU is within the tomographic image using the transducers VB, as illustrated in FIG. 4B. On the other hand, the inserted puncture needle 3 can be captured much faster than when a normal ultrasound probe is used in the tomographic image using the transducers VA (or the transducers VC). As an example, consider a case where the puncture needle 3 has been inserted into a target having a depth of 1 cm at an insertion angle of 45 degrees. If the width of the ultrasound beam by the transducers VB is 1.8 mm, the puncture needle is first reflected approximately 1 mm before the target in the normal ultrasound probe while being able to be confirmed approximately 4 mm before the target in the ultrasound probe 2 according to the present embodiment. Thus, if the crossing method according to the present embodiment is performed, a position of the puncture needle 3 can be confirmed significantly before the target T, and puncture work can be made easy.

A transmission/receiving sequence of the transducers 210 according to the present invention will be described below with reference to FIG. 3. As described above, in a configuration using the acoustic lens 220, the transducers VA, VB, and VC, and the switches SWA, SWB, and SWC, ultrasound is transmitted and received using the transducers VA and VB to obtain a reflection wave (echo) of the puncture needle 3, which has deviated from the ultrasound beam Bb formed by the transducers VB. However, transducers V1$a$, V1$b$, V1$c$, V2$a$, V2$b$, V2$c$, V3$a$, V3$b$, V3$c$, . . . can be subjected in this order to scanning (ultrasound transmission/receiving) in this case, for example. The scanning sequence is stored in the switching setter 24.

However, the number of times of transmission/receiving increases to three times in this case. Accordingly, a frame rate for B mode tomographic image display decreases to one-third. Therefore, the transducers V1$a$, V1$b$, V1$c$, V2$b$, V3$a$, V3$b$, V3$c$, V4$b$, V5$a$, V5$b$, V5$c$, . . . are scanned in this order, for example, by thinning out the scanning of the transducers VA and VC for capturing the puncture needle 3 so that the frame rate can be inhibited from decreasing. Although a case where one transducer is used for scanning in the long axis direction for simplicity has been described above, a plurality of transducers are actually used to form a transmission/receiving beam in the long axis direction. In addition, an already known method for increasing the frame rate by using parallel receiving in the long axis direction, for example, can also be applied.

Then, an outer shape of the ultrasound probe 2 will be described with reference to FIG. 6A, FIG. 6B, and FIG. 7. As illustrated in FIG. 6A and FIG. 6B, identifiers 26A and 26C are respectively formed on the front and the back of the case 25 in the outer shape of the ultrasound probe 2. The case 25 stores components such as the transducers 210, the acoustic lens 220, the switching element 230, and the switching setter 24. Particularly in the short axis direction on the front and the back of the ultrasound probe 2, the transducers VA, VB, and VC illustrated in FIG. 3 are arranged and stored. The identifier 26A formed on the front side of the case 25 is a section painted with a red paint as a color corresponding to the transducers VA on the front side in FIG. 3. The identifier 26C formed on the back side of the case 25 is a section painted with a green paint as a color corresponding to the transducers VC on the back side in FIG. 3. The identifiers 26A and 26C may be respectively configured by red and green seals or covers (adapters) having red and green portions detachably attached to the case 25. Further, the identifiers 26A and 26C may be configured to be identifiable by each other by feeling with an operator's hand or may be configured to form the identifier 26A as a projection and form the identifier 26C as a recess, for example.

On FIG. 6A, FIG. 6B, and FIG. 7, a red color is represented by a "shading pattern", and a green color is represented by "hatching". The colors are similarly represented in FIG. 10A, FIG. 10B, FIG. 11, FIG. 12, FIG. 14A, and FIG. 14B. A blue color corresponding to the transducers VB, described below, is represented by a "lattice pattern".

The operator can visually recognize the identifiers 26A and 26C in both the parallel method and the crossing method as the puncture method. However, in the parallel method, the operator may not easily visually recognize the identifiers 26A and 26C. Therefore, the ultrasound probe 2 may be replaced with an ultrasound probe 2D illustrated in FIG. 7.

Although the ultrasound probe 2D is similar to the ultrasound probe 2, a case 25 includes identifiers 26A1 and 26C1 instead of the identifiers 26A and 26C. Although the ultrasound probe 2D includes a projection 27 and a recess 28 in the case 25, the ultrasound probe 2 may also similarly include a projection and a recess.

The identifier 26A1 is formed on a front surface and a side surface of the case 25, and is a section painted with a red paint as a color corresponding to the transducers VA on the front side in FIG. 3. The identifier 26C1 is formed on a back surface and the side surface of the case 25, and is a section painted with a green paint as a color corresponding to the transducers VC on the front side in FIG. 3. The identifiers 26A1 and 26C1 may be respectively seals in red and green, for example. Further, the identifiers 26A1 and 26C1 may be configured to be also identifiable by each other by feeling with an operator's hand or may be configured to form the identifier 26A1 as a projection and form the identifier 26C1 as a recess, for example.

The projection 27 is a projection which connects an adapter in the ultrasound probe. The recess 28 may be a recess or a projection which recognizes a scanning direction by feeling with an operator's hand, for example.

The identifiers 26A1 and 26C1 can be visually recognized from not only the front and back sides but also the side surface by the operator. Accordingly, the operator can visually recognize the identifiers 26A and 26C in not only the crossing method but also the parallel method.

Figure 9A:
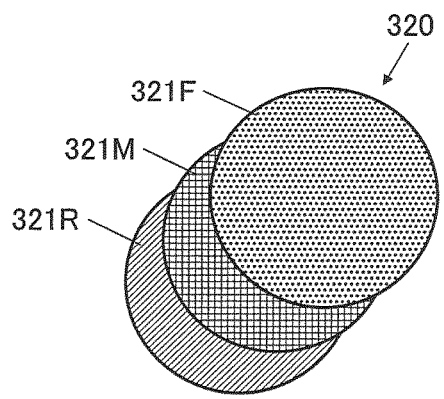
FIG. 9A is a diagram illustrating an identification mark the front side of which is red in the embodiment.
Figure 9B:
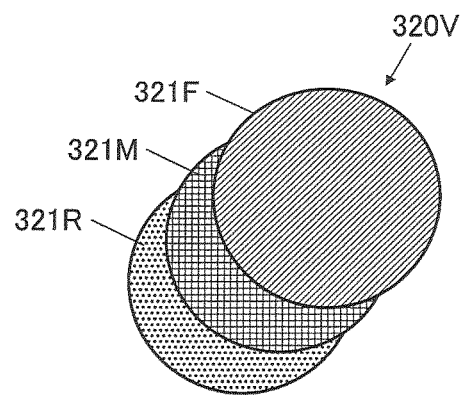
FIG. 9B is a diagram illustrating an identification mark the front side of which is green in the embodiment.
Figure 10A:
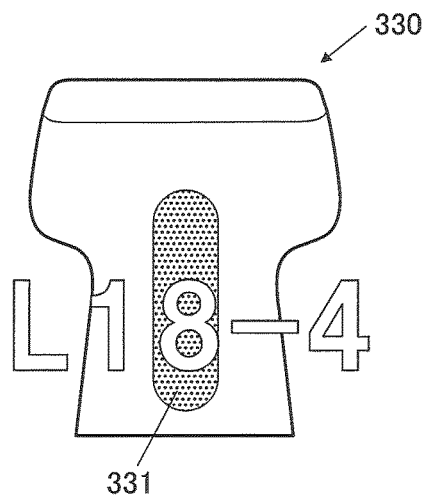
FIG. 10A is a diagram illustrating a probe mark the front side of which is red.
Figure 10B:
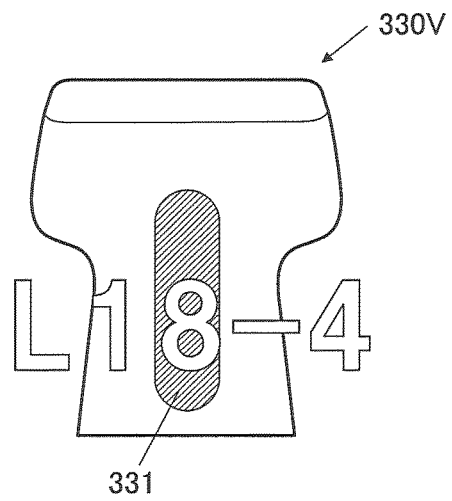
FIG. 10B is a diagram illustrating a probe mark the front side of which is green.

An operation of the ultrasound diagnostic apparatus U will be described below with reference to FIG. 8 to FIG. 11. FIG. 8 is a flowchart illustrating puncture needle image display processing. FIG. 9A is a diagram illustrating an identification mark 320 the front side of which is red in the present embodiment. FIG. 9B is a diagram illustrating an identification mark 320V the front side of which is green in the present embodiment. FIG. 10A is a diagram illustrating a probe mark 330 the front side of which is red. FIG. 10B is a diagram illustrating a probe mark 330V the front side of which is green. FIG. 11 is a diagram illustrating an ultrasound diagnostic screen 300 in the present embodiment.

Puncture needle image display processing performed by the ultrasound diagnostic apparatus U will be described with reference to FIG. 8. The puncture needle image display processing is processing for subjecting, when an operator such as an engineer or a doctor performs puncture work for inserting the puncture needle 3 into the target T as an object the tissue of which is to be acquired by puncturing the subject SU, for example, a B mode tomographic image of the puncture needle 3 within the subject to live display to assist in the puncture work.

An operator such as a doctor previously waits in a consultation room where the ultrasound diagnostic apparatus U is provided, and a patient as the subject SU enters the consultation room and lies down on a bed, and is ready for puncture work using the puncture needle 3, for example. In the ultrasound diagnostic apparatus U, the controller 11 performs puncture needle image display processing according to a puncture needle image display program stored in the ROM using receiving of respective instructions to input various types of setting information such as a frame rate in the puncture needle image display processing and execute the puncture needle image display processing from the operator via the operation input unit 18 as a trigger.

First, the controller 11 generates an initial identification mark and probe mark, and sets the generated marks for display (step S10). The identification mark is a display mark for identifying which of colors respectively used to color partial needle images corresponds to each of the front and the back of each of ultrasound images, which are used to insert the puncture needle, displayed side by side. Display colors (representations) of the partial needle images are set to a red color, a blue color, and a green color, respectively, as representations corresponding to the transducers VA, VB, and VC. The red color and the green color as the representations corresponding to the transducers VA and VC also respectively correspond to the identifiers 26A and 26C in the ultrasound probe 2. In step S10, the identification mark 320 illustrated in FIG. 9A, for example, is generated.

The identification mark 320 includes a front-side identifier 321F representing the front side of the ultrasound image, a center identifier 321M representing the center (middle) of the ultrasound image, and a back-side identifier 321R representing the back side of the ultrasound image. In the identification mark 320, the front-side identifier 321F is set to a red color, the center identifier 321M is set to a blue color, and the back-side identifier 321R is set to a green color.

The probe mark is a display mark for representing the type of the ultrasound probe 2, and indicates to which of the front and back sides of the ultrasound probe 2 the front side of each of the ultrasound images displayed side by side corresponds. In step S10, the probe mark 330 illustrated in FIG. 10A, for example, is generated.

The probe mark 330 includes an identifier 331 in addition to information representing the type of the ultrasound probe 2. In the probe mark 330 illustrated in FIG. 10A, the identifier 331 is set to a red color corresponding to the identifiers 26A in the ultrasound probe 2.

The controller 11 starts to cause the transmission driver 12 to generate a driving signal and input the driving signal to each transducer of the transducers VA, VB, and VC by switching the switching element 230 corresponding to the transmission/receiving sequence stored in the switching setter 24 via the transmission/receiving switcher 14 to emit transmission ultrasound and receive reflection ultrasound (echo), and causes the receiving processor 13 to acquire a receiving signal via the transmission/receiving switcher 14 (step S11). As the receiving signal obtained in step S11, receiving signals for each frame at the same time respectively corresponding to the transducers VA, VB, and VC are acquired in order corresponding to the transmission/receiving sequence.

The controller 11 causes the image generator 15 to generate B mode image data in one frame from the receiving signal corresponding to the transducers VA inputted from the receiving processor 13 in step S11 (step S12). The controller 11 causes the puncture needle identifier 162 to emphasize and extract a partial needle image of the puncture needle 3 from B mode image data corresponding to the transducers VA generated in step S12 (discard a portion other than the partial needle image) (step S13). The controller 11 causes the puncture needle identifier 162 to color the partial needle image in the image data generated in step S13 in a red color representing the transducers VA (step S14).

The controller 11 causes the image generator 15 to generate B mode image data in one frame from the receiving signal corresponding to the transducers VC inputted from the receiving processor 13 in step S11 (step S15). The B mode image data generated in step S15 becomes a frame at the same time as the B mode image data generated in step S12. The controller 11 causes the puncture needle identifier 162 to emphasize and extract a partial needle image of the puncture needle 3 from the B mode image data corresponding to the transducers VC generated in step S15 (step S16). The controller 11 causes the puncture needle identifier 162 to color the partial needle image in the image data generated in step S16 in a green color representing the transducers VC (step S17).

The controller 11 causes the image generator 15 to generate B mode image data in one frame from the receiving signal corresponding to the transducers VB inputted from the receiving processor 13 in step S11 (step S18). The B mode image data generated in step S18 becomes a frame at the same time as the B mode image data respectively generated in steps S12 and S15. The controller 11 causes the puncture needle identifier 162 to emphasize and extract a partial needle image of the puncture needle 3 from the B mode image data corresponding to the transducers VB generated in step S18 (step S19). The controller 11 causes the puncture needle identifier 162 to color the partial needle image in the image data generated in step S19 in a blue color representing the transducers VB (step S20).

In steps S14, S17, and S20, which of the transducers VA, VB, and VC has obtained the partial needle image is determined by making colors as the type of representation different. A combination of the colors in steps S14, S17, and S20 is one example, and is not limited to this. For example, a gradation like green-blue-violet may be used. Further, the type of representation which can be identified for each of the partial needle images may be changed to another type. Examples of the representation which can be identified for each of the partial needle images may include a configuration in which the partial needle images are made different in saturation and luminance, a configuration in which the partial needle images are made different in presence or absence of flashing, gap, and the like, or a configuration obtained by combining a plurality of types of representations. The identifiers 26A and 26C (identifiers 26A1 and 26C1), the identification mark 320, and the probe mark 330 are set to correspond to the representation of each of the partial needle images.

In steps S11, S12, S15, and S18, processing corresponding to each of the types of setting information first inputted is performed. A configuration in which various types of setting information are changed and inputted, as needed, from the operator via the operation input unit 18 during execution of the puncture needle image display processing may be used. A configuration in which the respective representations (colors) of the partial needle images in steps S14, S17, and S20 are inputted as various types of setting information from the operator via the operation input unit 18 may be used.

After step S18 is executed, the controller 11 causes the image generator 15 to acquire the normal B mode image data in one frame generated in step S11 (step S21). The controller 11 causes the image processor 16 to synthesize the partial needle image in red generated in step S14, the partial needle image in green generated in step S17, the partial needle image in blue generated in step S20, and the B mode image data in one frame acquired in step S21, to generate composite image data in one frame (step S22).

The controller 11 determines whether an operation input for right-and-left inversion or up-and-down inversion of an ultrasound image has been provided from the operator via the operation input unit 18 (step S23). When the ultrasound image is subjected to the right-and-left inversion or the up-and-down inversion, the front side and the back side of the ultrasound image are exchanged with each other. If the operation input for the right-and-left inversion or the up-and-down inversion is provided (YES in step S23), the controller 11 changes the identification mark and the probe mark which are being set for display to an identification mark and a probe mark after the inversion and sets the marks for display (step S24). If the identification mark 320 and the probe mark 330 have been set for display immediately before in step S24, the identification mark 320 and the probe mark 330 are respectively changed to the identification mark 320V illustrated in FIG. 9B and the probe mark 330V illustrated in FIG. 10B.

The identification mark 320V includes a front-side identifier 321F set in green, a center identifier 321M set in blue, and a back-side identifier 321R set in red. The probe mark 330V includes an identifier 331 set in green corresponding to the identifier 26A in the ultrasound probe 2. If the identification mark 320V and the probe mark 330V have been set for display immediately before in step S24, the identification mark 320V and the probe mark 330V are respectively changed to the identification mark 320 and the probe mark 330.

The identification marks 320 and 320V are not respectively limited to configurations illustrated in FIG. 9A and FIG. 9B. For example, the identification marks 320 and 320V may each have a configuration including only the front-side identifier 321F. The probe marks 330 and 330V are not respectively limited to configurations illustrated in FIG. 10A and FIG. 10B.

The controller 11 causes the image processor 16 to invert (or not to invert) the composite image data of the ultrasound images generated in step S22 right-and-left or up-and-down, as needed, depending on the presence or absence and the content of an inversion operation, and to display ultrasound diagnostic screen data including the ultrasound images in the composite image data and the identification mark and the probe mark which are being set for display on the output display 19 (step S25). If the operation input for the right-and-left inversion or the up-and-down inversion is not provided (NO in step S23), the processing proceeds to step S25.

In step S25, the ultrasound diagnostic screen 300 illustrated in FIG. 11 is displayed, for example. The ultrasound diagnostic screen 300 includes an ultrasound image 310, an identification mark 320, and a probe mark 330. The ultrasound image 310 includes partial needle images 311A, 311B, and 311C by the crossing method. The partial needle image 311A is colored in red, the partial needle image 311B is colored in blue, and the partial needle image 311C is colored in green. In the ultrasound image 310, an image portion other than the partial needle images 311A, 311B, and 311C is represented in white to make the partial needle images easy to see in FIG. 11. The same is true for an ultrasound image 310E illustrated in FIG. 12, described below. Visual recognition of the identification mark 320 and the probe mark 330 enables the operator to easily recognize that the partial needle image 311A in red is at a position on the front side of the ultrasound image 310, the partial needle image 311B in blue is at an intermediate position in a depth direction of the ultrasound image 310, and the partial needle image 311C in green is at a position on the back side of the ultrasound image 310.

The puncture needle image display processing preferably improves a depth depiction capability, although it uses all the transducers VA, VB, and VC for ultrasound image generation.

A method for depicting a relatively shallow site using the transducers at the center in the short axis direction among the plurality of transducers two-dimensionally arranged and depicting a relatively deep portion using all the transducers in the short axis direction has already been known. In the ultrasound probe 2, a focal length of an ultrasound beam (set as Babc) generated using all the transducers VA, VB, and VC in the short axis direction and the acoustic lens 220 is larger than a focal length of an ultrasound beam Bb generated using the transducers VB at the center in the short axis direction and the lens portion 221B in the acoustic lens 220.

If a relatively deep site is depicted using the ultrasound probe 2, it is desirable that an ultrasound beam (set as Bac) passes through the center in the entire short axis direction (a position of the ultrasound beam Bb corresponding to the transducers VB) at a depth at which depiction is to be performed for the lens portions 221A and 221C respectively corresponding to the transducers VA and VC and that the lens portions 221A and 221C are made to respectively have such curvatures that the ultrasound beam Babc focuses at a depth at which depiction is to be performed. The depth at which depiction is to be performed becomes larger than a predetermined depth at which the ultrasound beams Ba, Bb, and Bc respectively corresponding to the transducers VA, VB, and VC become exclusive.

As described above, according to the present embodiment, the ultrasound diagnostic apparatus U includes the ultrasound probe 2 including the plurality of transducers 210, which are arranged in the plurality of columns in the long axis direction arranged in the short axis direction and transmit and receive ultrasound and the switching element 230 which switches on and off of input of a driving signal to the transducers in each of the columns and output of a receiving signal. The ultrasound diagnostic apparatus U also includes the transmission driver 12 which outputs a driving signal to the transducers 210 in each of the columns in the ultrasound probe 2 via the switching by the switching element 230, the receiving processor 13 which acquires a receiving signal corresponding to the transducers 210 in each of columns from the ultrasound probe 2 via the switching by the switching element 230, the image generator 15 which generates ultrasound image data corresponding to each of the columns from the receiving signal corresponding to each of the column, the image processor 16 which makes partial needle images of the puncture needle 3 as a recognition object of the plurality of ultrasound image data have representations (colors) separately identifiable in each of the columns and synthesizes the plurality of ultrasound image data including the partial needle images to generate a composite image data, and the controller 11 which generates the identification mark 320 or 320V as first identification information indicating to which position in the depth direction of a composite image represented by the composite image data each of the representations (colors) of the partial needle images in the composite image data corresponds and displays the identification mark 320 or 320V and the composite image data, which are generated, on the output display 19.

Therefore, the operator can intuitively and easily recognize positions (positions on the front side, in the middle, and on the back side) in the depth direction of the puncture needle 3 as a recognition object by visual observation using the partial needle images in each of the colors in the ultrasound image and the identification mark 320 or 320V.

The ultrasound probe 2 includes the identifiers 26A and 26C which represent the representation of the partial needle image corresponding to a position in the short axis direction. Therefore, the operator can intuitively and easily recognize the position in the depth direction of the puncture needle 3 as a recognition object by visual observation to associate the position with positions (positions on the front side and the back side) in the short axis direction of the ultrasound probe 2 using the partial needle images in each of the colors in the ultrasound image and the identifiers 26A and 26C.

The identifiers 26A and 26C are respectively arranged at the positions on the front side and the back side of the ultrasound probe 2. Therefore, in the crossing method and the parallel method as the puncture method, the operator can intuitively and easily recognize the position in the depth direction of the puncture needle 3 by visual observation to associate the position with the position in the short axis direction of the ultrasound probe 2.

The identifiers 26A1 and 26C1 are respectively arranged at the positions on the front side and the side surface and the back side and the side surface of the ultrasound probe 2D. Therefore, in the parallel method as the puncture method, the operator can intuitively and easily recognize the position in the depth direction of the puncture needle 3 by visual observation to associate the position with the position in the short axis direction of the ultrasound probe 2.

The controller 11 generates the probe mark 330 or 330V as the second identification information in which the representation (color) of each of the partial needle images represents the corresponding position in the short axis direction of the ultrasound probe 2. The controller 11 displays the identification mark 320 or 320V, the probe mark 330 or 330V, and the composite image data which have been generated on the output display 19. Therefore, the probe mark 330 or 330V enables the operator to intuitively and easily recognize the position in the depth direction of the puncture needle 3 by visual observation to associate the position with the position in the short axis direction of the ultrasound probe 2.

The ultrasound diagnostic apparatus U includes the operation input unit 18 which accepts the operation input for the right-and-left inversion or the up-and-down inversion of the ultrasound image. The image processor 16 inverts the composite image represented by the composite image data in response to the operation input for the right-and-left inversion or the up-and-down inversion. The controller 11 reverses the depth direction of the identification mark to change the representation (color) in response to the operation input for the right-and-left inversion or the up-and-down inversion (from the identification mark 320 to the identification mark 320V and from the identification mark 320V to the identification mark 320). Therefore, if the right-and-left inversion or the up-and-down inversion of the ultrasound image is performed, the operator can also intuitively and easily recognize the position in the depth direction of the puncture needle 3 by visual observation using the partial needle images in each of the colors in the ultrasound image and the identification mark 320 or 320V.

(First Modification)

A first modification to the abovementioned embodiment will be described with reference to FIG. 12. Similar portions to those in the abovementioned embodiment are assigned the same reference numerals, and hence description thereof is not repeated. FIG. 12 is a diagram illustrating an ultrasound diagnostic screen 300E according to the modification.

As an apparatus configuration in the modification, an ultrasound diagnostic apparatus U is used, like in the abovementioned embodiment. The puncture needle image display processing illustrated in FIG. 8 is performed as an operation of the ultrasound diagnostic apparatus U. However, instruction information indicating that a partial needle image corresponding to transducers VB is neither emphasized nor colored in blue is inputted from an operator via an operation input unit 18 before the start of the execution of the puncture needle image display processing, and steps S19 and S20 are not executed in response to the instruction information after the start of the execution of the puncture needle image display processing.

The ultrasound diagnostic screen 300E illustrated in FIG. 12, for example, is displayed in step S25 by the puncture needle image display processing according to the modification. The ultrasound diagnostic screen 300E includes an ultrasound image 310E, an identification mark 320E, and a probe mark 330. Although the identification mark 320E is similar to the identification mark 320, a center identifier 321M is not colored in blue. The ultrasound image 310E includes partial needle images 311A, 311B1, and 311C by a crossing method. The partial needle image 311B1 is neither emphasized nor colored. Visual recognition of the identification mark 320E and the probe mark 330 enables the operator to more easily recognize that the partial needle image 311A in red is on the front side of the ultrasound image 310E and the partial needle image 311C in green is on the back side of the ultrasound image 310E. Then, it is checked whether the processing has been finished (step S26), and if yes, the process is ended, and if no, the step S11 is repeated.

As described above, according to the modification, a similar effect to the effect in the abovementioned embodiment is produced while an image processor 16 neither emphasizes nor sets a representation of the partial needle image of the puncture needle 3 as a recognition object in ultrasound image data corresponding to at least one of columns (the transducers VB) positioned at the center in a short axis direction. Therefore, when the puncture needle 3 as a recognition object does not deviate from the column (the transducers VB) at the center, a needle tip can be cleanly displayed, and the operator can easily recognize the needle tip by visual observation. When the puncture needle 3 has deviated, the operator can easily recognize the needle tip by visual observation.

(Second Modification)

Figure 13A:
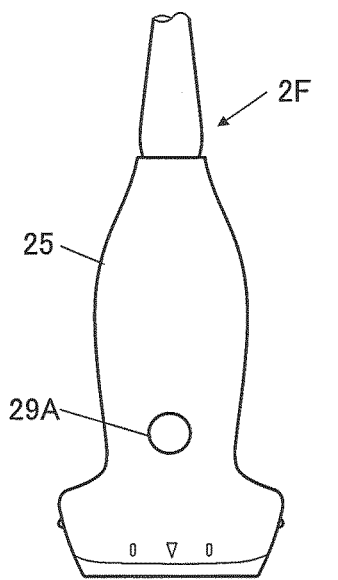
FIG. 13A is a plan view of a front surface of an ultrasound probe according to a second modification.
Figure 13B:
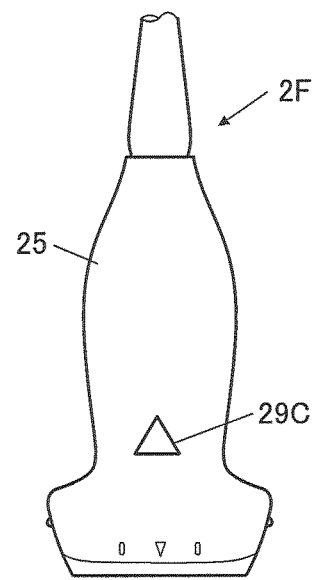
FIG. 13B is a plan view of a back surface of the ultrasound probe according to the second modification.
Figure 14A:
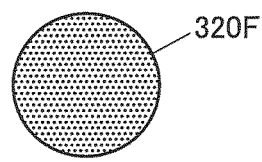
FIG. 14A is a diagram illustrating an identification mark the front side of which is red in the second modification.
Figure 14B:
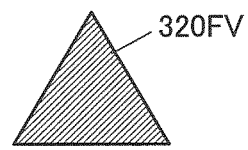
FIG. 14B is a diagram illustrating an identification mark the front side of which is green in the second modification.

A second modification to the abovementioned embodiment will be described below with reference to FIG. 13A to FIG. 14B. FIG. 13A is a plan view of a front surface of an ultrasound probe 2F according to the modification. FIG. 13B is a plan view of a back surface of the ultrasound probe 2F according to the modification. FIG. 14A is a diagram illustrating an identification mark 320F the front side of which is red in the modification. FIG. 14B is a diagram illustrating an identification mark 320FV the front side of which is green in the modification.

Although the ultrasound diagnostic apparatus U is used, like in the abovementioned embodiment, as an apparatus configuration in the modification, the ultrasound probe 2 is replaced with the ultrasound probe 2F illustrated in FIG. 13A and FIG. 13B.

Although the ultrasound probe 2F is substantially similar to the ultrasound probe 2, identifiers 29A and 29C are respectively formed on the front and back sides of a case 25. As illustrated in FIG. 13A, the identifier 29A formed on the front side of the case 25 is a section where a mark "○" is formed as a mark corresponding to the transducers VA on the front side in FIG. 3. The identifier 29A has a shape in which the operator can visually recognize the mark "○", and more preferably has a shape in which the operator can recognize the mark "○" by feeling with a hand.

As illustrated in FIG. 13B, the identifier 29C formed on the back side of the case 25 in the ultrasound probe 2F is a section where a mark "Δ" is formed as a mark corresponding to the transducers VC on the back side in FIG. 3. The identifier 29C has a shape in which the operation can visually recognize the mark "Δ", and more preferably has a shape in which the operator can recognize the mark "Δ" by feeling with a hand. It is easier to form the identifiers 29A and 29C than to color the case 25 in the ultrasound probe 2 by the identifiers 29A and 29C.

As an operation of the ultrasound diagnostic apparatus U according to the modification, the puncture needle image display processing illustrated in FIG. 8 is performed. However, the identification mark 320 is replaced with an identification mark 320F illustrated in FIG. 14A, and the identification mark 320V is replaced with an identification mark 320FV illustrated in FIG. 14B. The identification mark 320F has a shape of "○" corresponding to the shape of the identifier 29A on the front side of the case 25 in the ultrasound probe 2F, and is set to a red color corresponding to a color of a partial needle image corresponding to the transducers VA. The identification mark 320FV has a shape of "Δ" corresponding to the shape of the identifier 29A on the back side of the case 25 in the ultrasound probe 2F, and is set to a green color corresponding to a color of a partial needle image corresponding to the transducers VC.

As described above, according to the modification, a similar effect to the effect in the abovementioned embodiment is produced while the identifiers 29A and 29C can be easily formed in the ultrasound probe 2F.

Description in the abovementioned embodiment is one example of an appropriate ultrasound diagnostic apparatus according to the present invention, and the present invention is not limited to this.

For example, the configurations in at least two of the embodiment and the modifications, described above, may be combined, as needed. Although the ultrasound diagnostic apparatus U is configured to generate and display B mode image data as ultrasound image data in the embodiment and the modifications, described above, the present invention is not limited to this. The ultrasound diagnostic apparatus U may be configured to generate and display tomographic image data in another mode as ultrasound image data.

Although the ultrasound probe 2 includes the identifiers 26A and 26C each having a color in the ultrasound diagnostic apparatus U in the embodiment and the modifications, described above, the present invention is not limited to this. Some of operators cannot easily visually recognize the respective colors of the identifiers 26A and 26C due to visual impairment such as amblyopia. Therefore, the ultrasound probe 2 may include an identifier which causes a light emitter such as an LED (light emitting diode) to emit light in red on the front side of the case 25 and an identifier which causes the light emitter to emit light in green on the back side of the case 25, for example.

Although the ultrasound probe 2 in which the plurality of transducers in the long axis direction in three columns are arranged in the short axis direction has been described in the embodiment and the modifications, described above, the present invention is not limited to this. The number of exclusive regions can also be increased by making the number of divisions (the number of transducers) in the short axis direction larger, for example, increasing the three columns to five columns, seven columns, . . . in the short axis direction or simultaneously using the plurality of transducers, for example.

Although the partial images of the puncture needle 3 as a treatment instrument as a recognition object are extracted from the ultrasound image data and colored in the embodiment and the modifications, described above, the present invention is not limited to this. For example, a configuration in which a site such as a blood vessel within a subject is set as a recognition object and partial images of the site are extracted from ultrasound image data and colored (are made to respectively have representations separately identifiable in each of the columns) can also be used, and pseudo (simple) three-dimensional display can also be performed.

Although the ultrasound probe 2 includes the identifiers 26A (26A1, 29A) and 26C (26C1, 29C) in the ultrasound diagnostic apparatus U in the embodiment and the modifications, described above, the present invention is not limited to this. For example, the ultrasound probe 2 may include the identifier 26A (26A1, 29A) or the identifier 26C (26C1, 29C).

Although all display in a plurality of colors of the partial images of the puncture needle 3, provision of the identifiers 26A and 26C in the ultrasound probe 2, display of the identification marks 320 and 320V, and display of the probe marks 330 and 330V are combined in the ultrasound diagnostic apparatus U in the abovementioned embodiment, the present invention is not limited to this. For example, display in a plurality of colors of the partial images of the puncture needle 3 and display of the identification marks 320 and 320V may be combined in the ultrasound diagnostic apparatus U. Display in a plurality of colors of the partial images of the puncture needle 3 and provision of the identifiers 26A and 26C in the ultrasound probe 2 may be combined in the ultrasound diagnostic apparatus U. Display in a plurality of colors of the partial images of the puncture needle 3, provision of the identifiers 26A and 26C in the ultrasound probe 2, and display of the identification marks 320 and 320V or the probe marks 330 and 330V may be combined in the ultrasound diagnostic apparatus U. In this configuration, the probe marks 330 and 330V each function as first identification information.

Particularly, provision of the identifiers 26A and 26C in the ultrasound probe 2 and display of the identification marks 320 and 320V or display of the probe marks 330 and 330V may be combined in the ultrasound diagnostic apparatus U. This configuration is not limited to a configuration in which extracted partial images (partial needle images) are differently colored depending on each of columns in a short axis direction of transducers in an ultrasound probe to recognize a recognition object such as a puncture needle. The configuration will be described, assuming that the ultrasound diagnostic apparatus U displays a normal B mode ultrasound image. In Japanese Patent Laid-Open No. 2006-326204 and Japanese Patent Laid-Open No. 9-313491, an operator can only recognize the front and the back of an ultrasound probe, and cannot recognize a front-and-back relationship between an ultrasound image and an ultrasound probe.

On the other hand, the ultrasound diagnostic apparatus U is configured to include an ultrasound probe 2 including a plurality of transducers (e.g., transducers VB) which are arranged in at least one of columns in a long axis direction arranged in a short axis direction and transmit and receive ultrasound and identifiers (e.g., identifiers 26A and 26C) which respectively represent the front and the back in the short axis direction. The ultrasound diagnostic apparatus U may be configured to include a transmission driver 12 which outputs a driving signal to the transducers VB in the ultrasound probe 2, a receiving processor 13 which acquires a receiving signal from the transducers VB in the ultrasound probe 2, an image generator 15 which generates ultrasound image data from the receiving signal, and a controller 11 which generates an identification mark (e.g., an identification mark 320 or 320V excluding a center identifier 321M) or a probe mark (e.g., a probe mark 330 or 330V) as third identification information representing representations (colors) on the front and the back of the ultrasound probe 2 corresponding to the front and the back of the ultrasound image data, and displays the identification mark or probe mark and the ultrasound image data which have been generated on an output display 19.

The configuration enables an operator to intuitively and easily recognize the front and the back of the ultrasound image by visual observation by respectively associating the front and the back of the ultrasound image with positions (positions on the front side and the back side) in the short axis direction of the ultrasound probe 2 using the ultrasound image, the identifiers 26A and 26C, and the identification mark or the probe mark. The identification mark may have an identifier on the front side or the back side.

The ultrasound diagnostic apparatus U may be configured to include an operation input unit 18 which accepts an operation input for right-and-left inversion or up-and-down inversion of an ultrasound image and an image processor 16 which inverts an ultrasound image represented by ultrasound image data in response to the operation input for the right-and-left inversion or the up-and-down inversion. A controller 11 reverses representations (colors) on the front and the back of an identification mark (an identification mark 320 or 320V excluding a center identifier 321M) or a probe mark (e.g., a probe mark 330 or 330V) in response to the operation input for the right-and-left inversion or the up-and-down inversion. Therefore, even when the right-and-left inversion or the up-and-down inversion of the ultrasound image is performed, an operator can intuitively or easily recognize the front and the back of the ultrasound image by visual observation by respectively associating the front and the back of the ultrasound image with positions in a short axis direction of an ultrasound probe 2 using the ultrasound image, identifiers 26A and 26C, the identification mark or the probe mark.

A detailed configuration and a detailed operation of each of the units constituting the ultrasound diagnostic apparatus U according to the abovementioned embodiment can be appropriately chanted without departing from the spirit of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. An ultrasound diagnostic apparatus comprising:
an ultrasound probe including a plurality of transducer columns arrayed along a short axis direction, each transducer column including:
a plurality of transducers which are arranged in a long axis direction and transmit and receive ultrasound;
and a column switching element which independently switches on and off of input of a driving signal to the transducers in each of the columns and output of a receiving signal;
a transmitter which outputs the driving signal to the transducers in each of the columns in the ultrasound probe via the switching by the switching element;
a receiver which acquires the receiving signal corresponding to the transducers in each of the columns from the ultrasound probe via the switching by the switching element; and
a hardware processor which generates ultrasound image data corresponding to each of the columns from the receiving signal corresponding to the column, makes partial images of a recognition object in the plurality of ultrasound image data respectively having representations separately identifiable in each of the columns, synthesizes the plurality of ultrasound image data respectively including the partial images to generate composite image data, generates first identification information indicating to which position in a depth direction as the short axis direction of a composite image represented by the composite image data each of the representations of the partial images in the composite image data corresponds, and displays the generated first identification information and the generated composite image data in association with each other on a display.

2. The ultrasound diagnostic apparatus according to claim 1, wherein the ultrasound probe includes an identifier which represents the representation of the partial image corresponding to a position in the short axis direction.

3. The ultrasound diagnostic apparatus according to claim 2, wherein the identifier is arranged at a position or positions on either one or both of a front side and a back side of the ultrasound probe.

4. The ultrasound diagnostic apparatus according to claim 3, wherein the identifier is arranged at a position on a side surface of the ultrasound probe.

5. The ultrasound diagnostic apparatus according to claim 1, wherein the hardware processor generates second identification information in which the representation of each of the partial images represents a corresponding position in the short axis direction of the ultrasound probe, and displays the first identification information, the second identification information, and the composite image data, which are generated, on the display.

6. The ultrasound diagnostic apparatus according to claim 1, wherein the hardware processor neither emphasizes nor sets the representation of the partial image of the recognition object in the ultrasound image data corresponding to at least one of the columns positioned at a center in the short axis direction.

7. The ultrasound diagnostic apparatus according to claim 1, further comprising
    an operation unit which accepts an operation input for right-and-left inversion or up-and-down inversion of an ultrasound image,
    wherein the hardware processor inverts the composite image represented by the composite image data in response to the operation input for the right-and-left inversion or the up-and-down inversion, and reverses the depth direction in the first identification information in response to the operation input for the right-and-left inversion or the up-and-down inversion to change the representation.

8. An ultrasound diagnostic apparatus comprising:
    an ultrasound probe including a plurality of transducer columns arrayed along a short axis direction, each transducer column including:
        a plurality of transducers which are arranged in a long axis direction and transmit and receive ultrasound; and
        a column switching element which independently switches on and off of input of a driving signal to the transducers in each of the columns and output of a receiving signal;
    a transmitter which outputs the driving signal to the transducers in each of the columns in the ultrasound probe via the switching by the switching element;
    a receiver which acquires the receiving signal corresponding to the transducers in each of the columns from the ultrasound probe via the switching by the switching element; and
    a hardware processor which generates ultrasound image data corresponding to each of the columns from the receiving signal corresponding to the column, makes partial images of a recognition object in the plurality of ultrasound image data respectively have representations separately identifiable in each of the columns, synthesizes the plurality of ultrasound image data respectively including the partial images to generate composite image data, and displays the generated composite image data on a display,
    wherein the ultrasound probe includes an identifier which is arranged at a position in the short axis direction of the ultrasound probe and which represents the representation of the partial image corresponding to the position in the short axis direction at which the identifier is arranged.

9. An ultrasound diagnostic apparatus comprising:
    an ultrasound probe including a plurality of transducer columns arrayed along a short axis direction, each transducer column including;
        a plurality of transducers which are arranged in a long axis direction and transmit and receive ultrasound;
        a column switching element which independently switches on and off of input of a driving signal to the transducers in each of the columns and output of a receiving signal; and
        an identifier which represents a front and a back in the short axis direction;
    a transmitter which outputs a driving signal to the transducers in the ultrasound probe;
    a receiver which acquires a receiving signal from the transducers in the ultrasound probe; and
    a hardware processor which generates a plurality of ultrasound image data from the receiving signal, makes partial images of a recognition object in the plurality of ultrasound image data respectively having representations separately identifiable in each of the columns of the front and the back in the short axis direction, synthesizes the plurality of ultrasound image data respectively including the partial images to generate composite image data, generates identification information representing a representation of at least one of the front and the back of the ultrasound probe corresponding to a representation of a front and a back of the composite image data, and displays the generated third identification information and the generated ultrasound image data in association with each other, on a display.

10. The ultrasound diagnostic apparatus according to claim 9, further comprising
    an operation unit which accepts an operation input for right-and-left inversion or up-and-down inversion of an ultrasound image represented by the ultrasound image data,
    wherein the hardware processor inverts the ultrasound image in response to the operation input for the right-and-left inversion or the up-and-down inversion, and reverses the representations of the front and the back in the third identification information in response to the operation input for the right-and-left inversion or the up-and-down inversion.

\* \* \* \* \*